(12) United States Patent
Li et al.

(10) Patent No.: US 11,858,914 B2
(45) Date of Patent: Jan. 2, 2024

(54) PYRIMIDINE SMALL-MOLECULE COMPOUND AND APPLICATION THEREOF

(71) Applicant: WENZHOU MEDICAL UNIVERSITY, Wenzhou (CN)

(72) Inventors: Xiaokun Li, Wenzhou (CN); Zhiguo Liu, Wenzhou (CN); Li Lin, Wenzhou (CN); Xiaohui Zheng, Wenzhou (CN); Jianchang Qian, Wenzhou (CN)

(73) Assignee: WENZHOU MEDICAL UNIVERSITY, Wenzhou (CN)

( * ) Notice: Subject to any disclaimer, the term of this patent is extended or adjusted under 35 U.S.C. 154(b) by 0 days.

(21) Appl. No.: 18/331,758

(22) Filed: Jun. 8, 2023

(65) Prior Publication Data

US 2023/0312529 A1   Oct. 5, 2023

Related U.S. Application Data (63) Continuation of application No. PCT/CN2021/140401, filed on Dec. 22, 2021.

(51) Int. Cl.
| | |
|---|---|
| *C07D 401/14* | (2006.01) |
| *C07D 403/12* | (2006.01) |
| *A61P 27/02* | (2006.01) |
| *A61P 35/00* | (2006.01) |

(52) U.S. Cl.
CPC ............ *C07D 403/12* (2013.01); *A61P 27/02* (2018.01); *A61P 35/00* (2018.01); *C07D 401/14* (2013.01)

(58) Field of Classification Search
CPC .............................. C07D 401/14; C07D 403/12
See application file for complete search history.

(56) References Cited

U.S. PATENT DOCUMENTS

| | | |
|---|---|---|
| 2009/0054425 A1 | 2/2009 | Song et al. |
| 2018/0290984 A1 | 10/2018 | Schönbrunn et al. |

FOREIGN PATENT DOCUMENTS

| | | |
|---|---|---|
| CN | 102112131 A | 6/2011 |
| CN | 103626742 A | 3/2014 |
| CN | 106831730 A | 6/2017 |
| CN | 110669038 A | 1/2020 |
| CN | 110746402 A | 2/2020 |
| CN | 111423419 A | 7/2020 |
| WO | 2016022460 A1 | 2/2016 |
| WO | 2017066428 A1 | 4/2017 |

OTHER PUBLICATIONS

Internation Search Report of PCT/CN2021/140401, dated Mar. 15, 2022.

Liu, Qian et al., "A Novel Indazole Derivative, Compound Cyy-272, Attenuates LPS-Induced Acute Lung Injury by Inhibiting JNK Phosphorylation", Toxicology and Applied Pharmacology, vol. 428, Jul. 17, 2021, p. 115648, compound Cyy-272.

Chen, Lingfeng et al., "Structure-Based Design and Synthesis of 2,4-Diaminopyrimidines as EGFR L858R/T790M Selective Inhibitors for NSCLC", European Journal of Medicinal Chemistry, vol. 140, Sep. 20, 2017, pp. 510-527, compounds 14e, 15b, and 15c.

*Primary Examiner* — Brian E McDowell (57) ABSTRACT

Disclosed are a pyrimidine small-molecule compound and an application thereof. The pyrimidine small-molecule compound has efficient inhibitory activity towards PDGFRα and PDGFRβ kinases, but has relatively weak inhibitory activity towards other kinases. Therefore, the compound has very high selectivity and is capable of being used as a potential drug for resisting tumors or relieving ophthalmic diseases such as wet age-related macular degeneration or uveitis.

1 Claim, 2 Drawing Sheets

PYRIMIDINE SMALL-MOLECULE COMPOUND AND APPLICATION THEREOF

CROSS-REFERENCE TO RELATED APPLICATIONS

This application is a continuation of International Patent Application No. PCT/CN2021/140401 with a filing date of Dec. 22, 2021, designating the United States, now pending, and further claims priority to Chinese Patent Application No. 202110012605.2 with a filing date of Jan. 6, 2021. The content of the aforementioned applications, including any intervening amendments thereto, are incorporated herein by reference.

TECHNICAL FIELD

The present invention belongs to the field of biomedicine, and more particularly, relates to a pyrimidine small-molecule compound and a preparation method and application thereof.

BACKGROUND OF THE PRESENT INVENTION

Platelet-Derived Growth Factor Receptors (PDGFRs) have two subtypes of PDGFRα and PDGFRβ, which play an important role in the growth, development, vascular formation, and tissue wound repair of organisms. Under normal physiological conditions, PDGFRs signaling pathway is generally at rest in adults except during development and tissue trauma repair. Over-expression, gene mutation and gene rearrangement of PDGFRs may lead to abnormal activation of PDGFRs-mediated signaling pathway, and lead to a series of diseases such as fibrosis, tumor and various ophthalmic diseases, such as wet age-related macular degeneration (AMD) and uveitis, so PDGFRs have become important drug targets for the treatment of these diseases.

At present, selective inhibitors against PDGFRs include imatinib, CP-673451, etc. These inhibitors usually have a plurality of defects, such as poor kinase inhibitory activity, large toxic and side effects caused by multi-target inhibition, and easily caused drug resistance. Therefore, it is necessary to provide a class of inhibitors that selectively inhibit PDGFRα or PDGFRβ, and are double-targeted to PDGFRα and PDGFRβ, so as to provide research basis for precise targeted medical treatment.

SUMMARY OF PRESENT INVENTION

Through experiments, the inventors of the present invention found a selective PDGFRs inhibitor, which can effectively alleviate tumors and various ophthalmic diseases caused by high expression or mutation of PDGFRs, ABL or FLT3 genes.

The present invention adopts the following technical solutions:

A pyrimidine small-molecule compound is a compound represented by formula (I), (II) or (III), a salt thereof, a solvate thereof, a hydrate thereof or a prodrug thereof;

(I)

(II)

(III)

in formulas (I) to (III), $R_1$ is selected from H, —$CF_3$ or $C_1$-$C_5$ alkyl; $R_2$ is selected from H, —$CF_3$, $C_1$-$C_5$ alkyl, $C_1$-$C_5$ alkoxy, halogen or $C_1$-$C_5$ alkoxycarbonyl; or $R_1$ and $R_2$ form a five-membered ring with two C connecting $R_1$ and $R_2$;

$R_3$ is a substituted or unsubstituted aryl, and a substituent on the aryl is selected from $C_1$-$C_5$ alkyl; and $R_4$ is a substituted or unsubstituted aryl, a substituent on the aryl is one or more of $C_1$-$C_5$ alkyl, $C_1$-$C_5$ alkoxy, piperazinyl, substituted piperazinyl, 1,1-thiomorpholinyl, piperidinyl and substituted piperidinyl, and substituents on the piperazinyl and piperidinyl are selected from $C_1$-$C_5$ alkyl or halogen. Preferably, the aryl is phenyl.

Preferably, $R_1$ is selected from H, —$CF_3$ or methyl; $R_2$ is selected from H, —$CF_3$, methyl, methoxy, F, Cl and ethoxycarbonyl; or $R_1$ and $R_2$ form an S-containing five-membered ring with two C connecting $R_1$ and $R_2$.

Preferably, $R_3$ is a substituted or unsubstituted indolyl, a substituted or unsubstituted indazolyl, a substituted or unsubstituted quinoxalinyl, a substituted or unsubstituted quinolyl, and an indanyl; and substituents on the indolyl, the indazolyl, the quinoxalinyl and the quinolyl are methyl or ethyl.

Preferably, $R_4$ is a substituted or unsubstituted phenyl, a substituent on the phenyl one or more of is methyl, methoxy, piperazinyl, substituted piperazinyl, 1,1-thiomorpholinyl, piperidinyl or substituted piperidinyl, and substituents on the piperazinyl and piperidinyl are selected from methyl, F or Cl.

Preferably, the pyrimidine small-molecule compound is one of compound 3a, compound 3b, compound 3c, compound 3d, compound 3e, compound 3f, compound 3g, compound 3h, compound 3i, compound 5a, compound 5b, compound 5c, compound 5d, compound 5e, compound 5f, compound 5g, compound 5h, compound 5i, compound 5j, compound 5k, compound 6a, compound 6b, compound 6c, compound 6d, compound 6e, compound 6f, compound 6g, compound 6h, compound 6i, compound 6j, compound 6k, compound 6m, compound 6n, a salt thereof, a solvent compound thereof, a hydrate thereof, or a prodrug thereof, and a structural formula of the pyrimidine small-molecule compound is as follows:

3a

3b

-continued

3c

3d

3e

3f

5d

5e

5f

5g

5h

5i

5j

5k

6a

6b

6c

6d

6e

6f

6g

6h

The present invention further provides an application of the pyrimidine small-molecule compound, wherein the pyrimidine small-molecule compound is used for preparing PDGFRs, ABL or FLT3 inhibitors.

Preferably, the inhibitor is capable of efficiently inhibiting PDGFRα, PDGFRβ, ABL or FLT3, but has medium or weak inhibitory activity towards other kinases.

Preferably, the pyrimidine small-molecule compound is used for preparing an anti-tumor drug.

Preferably, the anti-tumor drug is used for inhibiting human adolescent osteosarcoma and blood tumor.

Preferably, the pyrimidine small-molecule compound is used for preparing a drug for treating an ophthalmic disease.

The drug is used for inhibiting hyperplasia of fundus blood vessels, thereby alleviating ophthalmic diseases such as wet age-related macular degeneration or uveitis.

The present invention further provides an application of the pyrimidine small-molecule compound, wherein the pyrimidine small-molecule compound is used for preparing an anti-tumor drug; and the anti-tumor drug is used for treating one or more of leukemia, colon cancer, rectal cancer, gastric cancer, breast cancer, ovarian cancer, choriocarcinoma, malignant mole, head and neck squamous cell carcinoma, skin cancer, liver cancer, bladder cancer, lung cancer, prostate cancer, uterine cancer, renal cancer and lymphoma.

Compared with the prior art, the present invention has the beneficial effects as follows.

(1) The pyrimidine small-molecule compound of the present invention has efficient inhibitory activity towards PDGFRα, PDGFRβ, ABL or FLT3β kinases, but has medium or weak inhibitory activity towards other kinases, thereby having very high selectivity.

(2) The pyrimidine small-molecule compound of the present invention has better anti-osteosarcoma and blood tumor effects, and is a potential anti-tumor drug.

(3) The pyrimidine small-molecule compound of the present invention can effectively inhibit hyperplasia of fundus blood vessels, thereby alleviating ophthalmic diseases such as wet age-related macular degeneration or uveitis.

DETAILED DESCRIPTION OF PREFERRED EMBODIMENTS

Example 1: Chemical Synthesis of Compound 3a-3i

The synthesis route was as follows:

The general process was as follows:

1a-1i was used as a raw material to undergo a nucleophilic substitution reaction with 6-aminoindazole to generate an intermediate 2a-2i. 4-(4-methylpiperazine)aniline and the obtained intermediate 2a-2i underwent a nucleophilic substitution reaction to generate a final product 3a-3i.

Taking the synthesis of a compound 3a for example, a specific process was as follows:

2,4-dichloro-5-fluoropyrimidine (333.94 mg, 2 mmol) and N, N-diisopropylethylamine (DIPEA) (516.96 mg, 4 mmol) were dissolved in DMF (4 mL) and cooled to 0° C. Then 6-aminoindazole (266.3 mg, 2 mmol) dissolved in DMF (2 mL) was added dropwise to the mixed solution. The reaction mixture was stirred at 0° C. for about 1 hour. Next, the ice bath was removed, the reaction mixture was stirred at room temperature, and the reaction was monitored by TLC. The resulting mixture was extracted with ethyl acetate (3×25 mL), washed with saturated salt solution, dried and concentrated by anhydrous $Na_2SO_4$, and then a product 2a was obtained by silica gel column chromatography.

Compound 2a (263.66 mg, 1 mmol) and 4-(4-methylpiperazine)aniline (191.27 mg, 1 mmol) were dissolved in methanol (4 mL), then added with trifluoroacetic acid (TFA) (148.56 v L, 2 mmol), heated to 80° C., and the reaction was monitored by TLC. After the reaction was completed, the mixture was cooled to room temperature, the resulting mixture was adjusted to be neutral with saturated sodium bicarbonate, extracted with ethyl acetate (3×25 mL), washed with saturated salt solution, dried and concentrated by anhydrous $Na_2SO_4$, and a final product 3a was obtained by silica gel column chromatography.

Characterization data of compound 3a-3i was as follows:

5-fluoro-$N^4$-(1H-indazol-6-yl)-$N^2$-(4-(4-methylpiperazine-1-yl) p henyl)pyrimidine-2,4-diamine (3a), yellow solid, yield: 26.9%. $^1$H NMR (500 MHz, DMSO-$d_6$) δ 12.93 (s, 1H), 9.41 (s, 1H), 8.99 (s, 1H), 8.08 (d, J=3.5 Hz, 1H), 8.01 (s, 1H), 7.91 (s, 1H), 7.69 (d, J=8.5 Hz, 1H), 7.52 (d, J=8.5 Hz, 3H), 6.81 (d, J=8.5 Hz, 2H), 3.06 (s, 4H), 2.57 (s, 4H), 2.30 (s, 3H). $^{13}$C NMR (126 MHz, DMSO-$d_6$) δ 170.28, 155.87, 149.81, 149.73, 145.77, 140.26, 139.40, 137.05, 133.30, 133.15, 120.02, 119.33, 116.55, 115.88, 101.58, 54.61, 48.85, 14.05; ESI-MS m/z: 419.2 (M+H)$^+$.

5-chloro-$N^4$-(1H-indazol-6-yl)-$N^2$-(4-(4-methylpiperazine-1-yl) p henyl)pyrimidine-2,4-diamine (3b) $^1$H NMR (400 MHz, DMSO-$d_6$) δ 9.06 (s, 1H), 8.89 (s, 1H), 8.10 (s, 1H), 8.04 (s, 1H), 7.76 (s, 1H), 7.71 (d, J=8.6 Hz, 1H), 7.42 (d, J=8.8 Hz, 2H), 7.36 (d, J=8.6 Hz, 1H), 6.69 (d, J=8.8 Hz, 2H), 5.76 (s, 1H), 2.99 (s, 4H), 2.44 (s, 4H), 2.21 (s, 3H). $^{13}$C NMR (100 MHz, DMSO-$d_6$) δ 158.40, 156.64, 155.15, 146.47, 137.26, 133.78, 133.03, 120.79, 120.44, 120.34, 118.62, 116.20, 104.46, 104.00, 103.67, 55.17, 49.34, 46.27.

$N^4$-(1H-indazol-6-yl)-$N^2$-(4-(4-methylpiperazine-1-yl) phenyl)-5-(trifluoromethyl)pyrimidine-2,4-diamine (3c), white Solid, yield: 16.5%. $^1$H NMR (400 MHz, DMSO-$d_6$) δ 9.70 (s, 1H), 8.63 (s, 1H), 8.33 (s, 1H), 7.92 (s, 1H), 7.72 (dd, J=5.6, 3.2 Hz, 1H), 7.68-7.65 (m, 1H), 7.48 (d, J=8.8 Hz, 1H), 7.29 (d, J=8.8 Hz, 3H), 7.01 (d, J=8.8 Hz, 2H), 3.18-3.14 (m, 4H), 2.51 (d, J=1.6 Hz, 4H), 2.24 (s, 3H). $^{13}$C NMR (126 MHz, DMSO-$d_6$) δ 166.94, 160.70, 155.18, 148.42, 140.43, 138.08, 133.18, 131.68, 131.47, 129.73, 128.62, 127.55, 126.84, 119.81, 118.54, 115.35, 99.13, 54.50, 48.25, 45.65; ESI-MS m/z: 469.2 (M+H)$^+$.

$N^4$-(1H-indazol-6-yl)-5-methyl-$N^2$-(4-(4-methylpiperazine-1-yl) p henyl)pyrimidine-2,4-diamine (3d), white solid, yield: 31.5%. $^1$H NMR (500 MHz, DMSO-$d_6$) δ 12.89 (s, 1H), 8.74 (s, 1H), 8.36 (s, 1H), 8.00 (s, 1H), 7.86 (s, 1H), 7.82 (s, 1H), 7.68 (d, J=9.0 Hz, 1H), 7.51 (d, J=9.0 Hz, 2H), 7.42 (d, J=9.0 Hz, 1H), 6.72 (d, J=9.0 Hz, 2H), 2.99 (d, J=4.0 Hz, 4H), 2.46 (d, J=4.5 Hz, 4H), 2.23 (s, 3H), 2.12 (s, 3H). $^{13}$C NMR (126 MHz, DMSO-$d_6$) δ 159.36, 158.45, 155.73, 145.35, 140.38, 138.06, 133.62, 133.23, 119.71, 119.18, 117.52, 115.93, 105.03, 102.29, 54.64, 48.98, 45.61, 13.49; ESI-MS m/z: 415.2 (M+H)$^+$.

$N^4$-(1H-indazol-6-yl)-5-methoxy-$N^2$-(4-(4-methylpiperazine-1-yl) phenyl)pyrimidine-2,4-diamine (3e) $^1$H NMR (400 MHz, DMSO-$d_6$) δ 8.77 (s, 1H), 8.65 (s, 1H), 7.96 (s, 2H), 7.83 (s, 1H), 7.65 (d, J=8.7 Hz, 1H), 7.55-7.53 (m, 3H), 6.79 (d, J=9.0 Hz, 2H), 3.86 (s, 3H), 3.01 (s, 4H), 2.45 (s, 4H), 2.22 (s, 3H). $^{13}$C NMR (100 MHz, DMSO-$d_6$) δ 154.60, 152.26, 145.77, 138.16, 137.40, 134.87, 134.48, 133.77, 120.40, 119.79, 119.69, 119.52, 117.10, 116.54, 101.56, 57.42, 55.25, 49.61, 46.27.

Ethyl-4-((1H-indazol-6-yl)amino)-2-((4-(4-methylpiperazine-1-yl)phenyl)amino)pyrimidine-5-carboxylate (3f), yellow solid, yield: 95.1%. $^1$H NMR (400 MHz, DMSO-d$_6$) δ 13.05 (s, 1H), 10.34 (s, 1H), 9.86 (s, 1H), 8.73 (s, 1H), 8.08 (s, 1H), 7.76 (d, J=8.4 Hz, 1H), 7.53 (d, J=5.6 Hz, 2H), 7.29 (d, J=7.3 Hz, 1H), 6.81 (s, 2H), 4.34 (q, J=6.8 Hz, 2H), 3.17 (s, 4H), 2.75 (s, 4H), 2.43 (s, 3H), 1.37 (t, J=7.0 Hz, 3H). $^{13}$C NMR (100 MHz, DMSO-d$_6$) δ 166.39, 160.64, 160.44, 153.10, 146.23, 140.24, 136.11, 136.03, 133.47, 133.43, 131.57, 121.48, 120.57, 115.83, 60.36, 53.65, 47.55, 44.23, 14.16; ESI-MS m/z: 473.2 (M+H)$^+$.

N$^4$-(1H-indazol-6-yl)-N$^2$-(4-(4-methylpiperazine-1-yl)phenyl)-6-(trifluoromethyl)pyrimidine-2,4-diamine (3g), yellow solid, yield: 50.7%. $^1$H NMR (500 MHz, DMSO-d$_6$) δ 13.07 (s, 1H), 9.47 (s, 1H), 8.81 (s, 1H), 8.31 (s, 1H), 8.08 (s, 1H), 7.74 (d, J=8.5 Hz, 1H), 7.57 (s, 1H), 7.26 (s, 2H), 7.17 (s, 1H), 6.43 (s, 2H), 2.93 (s, 4H), 2.41 (s, 4H), 2.20 (s, 3H). $^{13}$C NMR (126 MHz, DMSO-d$_6$) δ 160.52, 157.77, 155.55, 155.51, 146.34, 140.18, 136.35, 133.20, 131.54, 126.00, 123.86, 120.76, 120.73, 120.52, 119.94, 115.31, 54.58, 48.62, 45.70; ESI-MS m/z: 469.2 (M+H)$^+$.

N$^4$-(1H-indazol-6-yl) amino)-6-methyl-N$^2$-(4-(4-methylpiperazine-1-yl)phenyl)pyrimidine-2,4-diamine (3h), yellow liquid, yield: 29.3%. $^1$H NMR (500 MHz, DMSO-d$_6$) δ 12.76 (s, 1H), 9.24 (s, 1H), 8.85 (s, 1H), 7.96 (s, 1H), 7.82 (s, 1H), 7.64 (d, J=8.5 Hz, 1H), 7.60 (d, J=8.5 Hz, 2H), 7.32 (d, J=8.5 Hz, 1H), 6.84 (d, J=8.0 Hz, 2H), 6.07 (s, 1H), 3.05 (s, 4H), 2.50 (s, 4H), 2.24 (s, 3H), 2.20 (s, 3H). $^{13}$C NMR (126 MHz, DMSO-d$_6$) δ 164.46, 161.29, 159.59, 146.55, 140.88, 139.50, 133.04, 132.11, 121.71, 120.21, 119.76, 117.86, 116.03, 115.10, 97.80, 54.45, 48.48, 45.62, 23.61; ESI-MS m/z: 415.2 (M+H)$^+$.

N$^4$-(1H-indazol-6-yl) amino)-6-methyl-N$^2$-(4-(4-methylpiperazine-1-yl)phenyl)thiophene[2,3-d]pyrimidine-2,4-diamine (3i), $^1$H NMR (400 MHz, DMSO-d$_6$) δ 9.51 (s, 1H), 8.86 (s, 1H), 8.05 (d, J=5.4 Hz, 1H), 8.03 (s, 1H), 7.93 (s, 1H), 7.71 (d, J=8.7 Hz, 1H), 7.62 (d, J=9.0 Hz, 2H), 7.54-7.49 (m, 1H), 7.18 (d, J=5.4 Hz, 1H), 6.80 (d, J=9.0 Hz, 2H), 3.03 (s, 4H), 2.44 (s, 4H), 2.20 (S, 3H). $^{13}$C NMR (100 MHz, DMSO-d$_6$) δ 162.66, 158.62, 155.98, 146.08, 140.80, 137.97, 134.18, 134.11, 133.81, 123.85, 120.58, 120.51, 120.40, 119.98, 117.83, 116.43, 107.67, 103.16, 55.24, 49.54, 46.29.

Example 2: Chemical Synthesis of Compound 5a-5j

The synthesis route was as follows:

The general process was as follows:

2,4-dichloro-5-methylpyrimidine (1d) underwent a nucleophilic substitution reaction with various substituted amines to generate an intermediate 4a-4j. 4-(4-methylpiperazine)aniline and the obtained intermediate 4a-4j underwent a nucleophilic substitution reaction to generate a final product 5a-5j.

Taking the synthesis of a compound 5a for example, a specific process was as follows:

N, N-diisopropylethylamine (DIPEA) (516.96 mg, 4 mmol) was dissolved in DMF (4 mL) and cooled to 0° C. Then 5-aminoindole (266.3 mg, 2 mmol) dissolved in DMF (2 mL) was added dropwise to the mixed solution. The reaction mixture was stirred at 0° C. for about 1 hour. Next, the ice bath was removed, the reaction mixture was stirred at room temperature, and the reaction was monitored by TLC. After the reaction was completed, the resulting mixture was extracted with ethyl acetate (3×25 mL), washed with saturated salt solution, dried and concentrated by anhydrous Na$_2$SO$_4$, and an intermediate 4a was obtained by silica gel column chromatography. The intermediate 4a (258.7 mg, 1 mmol) and 4-(4-methylpiperazine)aniline (191.27 mg, 1 mmol) were dissolved in methanol (4 mL), then added with TFA (148.56 μl L, 2 mmol), heated to 80° C., and the reaction was monitored by TLC. After the reaction was completed, the mixture was cooled to room temperature, the resulting mixture was adjusted to be neutral with saturated sodium bicarbonate, extracted with ethyl acetate (3×25 mL), washed with saturated salt solution, dried and concentrated by anhydrous Na$_2$SO$_4$, and a final product 5a was obtained by silica gel column chromatography.

A structure and characterization data of the obtained compound 5a-5k were as follows:

N$^4$-(1H-indazol-5-yl) amino)-5-methyl-N$^2$-(4-(4-methylpiperazine-1-yl)phenyl)pyrimidine-2,4-diamine (5a), pink liquid, yield: 41.91%. $^1$H NMR (500 MHz, DMSO-d$_6$) δ 11.00 (s, 1H), 8.54 (s, 1H), 8.09 (s, 1H), 7.83 (s, 1H), 7.76 (s, 1H), 7.47 (d, J=9.0 Hz, 2H), 7.39-7.30 (m, 2H), 7.25 (d, J=8.5 Hz, 1H), 6.65 (d, J=9.0 Hz, 2H), 6.39 (s, 1H), 2.96 (d, J=4.5 Hz, 4H), 2.47-2.38 (m, 4H), 2.21 (s, 3H), 2.09 (s, 3H). $^{13}$C NMR (126 MHz, DMSO-d$_6$) δ 159.95, 158.57, 154.90, 145.17, 133.84, 133.01, 131.42, 127.55, 125.44, 119.65, 118.64, 115.98, 114.77, 110.70, 104.30, 101.05, 54.74, 49.16, 45.75, 13.52; ESI-MS m/z: 414.2 (M+H)$^+$.

N$^4$-(1H-indazol-4-yl) amino)-5-methyl-N$^2$-(4-(4-methylpiperazine-1-yl)phenyl)pyrimidine-2,4-diamine (5b), gray solid, yield: 74.49%. $^1$H NMR (400 MHz, DMSO-d$_6$) δ

11.15 (s, 1H), 8.60 (s, 1H), 8.08 (s, 1H), 7.85 (s, 1H), 7.43-7.35 (m, 3H), 7.31 (t, J=2.8 Hz, 1H), 7.26 (d, J=8.1 Hz, 1H), 7.12 (t, J=8.0 Hz, 1H), 6.65 (d, J=8.8 Hz, 2H), 6.49-6.33 (m, 1H), 3.02-2.96 (m, 4H), 2.50-2.44 (m, 4H), 2.25 (s, 3H), 2.19 (s, 3H). $^{13}$C NMR (126 MHz, DMSO-$d_6$) δ 159.94, 158.51, 155.20, 145.12, 136.81, 133.78, 131.53, 124.20, 123.06, 120.90, 119.42, 115.74, 114.12, 107.71, 104.64, 99.56, 54.67, 49.10, 45.67, 13.38; ESI-MS m/z: 414.2 (M+H)+.

5-methyl-$N^4$-(1-methyl-1H-indazol-5-yl)-$N^2$-(4-(4-methylpiperazine-1-yl)phenyl)pyrimidine-2,4-diamine (5c), gray solid, yield: 52.1%. $^1$H NMR (400 MHz, DMSO-$d_6$) δ 8.63 (s, 1H), 8.18 (s, 1H), 7.90 (d, J=2.0 Hz, 1H), 7.80 (s, 1H), 7.50 (d, J=9.2 Hz, 2H), 7.43 (d, J=8.8 Hz, 1H), 7.33 (dd, J=7.2, 2.8 Hz, 2H), 6.69 (d, J=9.2 Hz, 2H), 6.40 (d, J=2.8 Hz, 1H), 3.83 (s, 3H), 3.04-2.97 (m, 4H), 2.49-2.43 (m, 4H), 2.24 (s, 3H), 2.12 (s, 3H). $^{13}$C NMR (126 MHz, DMSO-$d_6$) δ 159.88, 158.55, 154.96, 145.17, 133.76, 133.55, 131.65, 129.71, 127.89, 119.73, 118.59, 115.82, 114.93, 109.00, 104.29, 100.22, 54.73, 49.02, 45.75, 32.51, 13.52; ESI-MS m/z: 428.6 (M+H)+.

$N^4$-(1H-indazol-5-yl) amino)-5-methyl-$N^2$-(4-(4-methylpiperazine-1-yl)phenyl)pyrimidine-2,4-diamine (5d), yellow oil, yield: 63.5%. $^1$H NMR (500 MHz, DMSO-$d_6$) δ 8.80 (s, 1H), 8.76 (d, J=3.5 Hz, 1H), 8.56 (s, 1H), 8.50 (s, 1H), 8.12 (d, J=8.0 Hz, 1H), 8.04 (dd, J=9.0, 2.0 Hz, 1H), 7.96-7.89 (m, 3H), 7.48 (d, J=8.5 Hz, 2H), 6.78 (d, J=9.0 Hz, 1H), 3.06-3.00 (m, 4H), 2.48-2.43 (m, 4H), 2.23 (s, 2H), 2.16 (s, 3H). $^{13}$C NMR (126 MHz, DMSO-$d_6$) δ 158.89, 158.64, 156.12, 148.42, 145.85, 144.42, 138.08, 135.19, 133.13, 128.64, 128.28, 125.73, 121.23, 120.85, 116.54, 115.85, 105.27, 54.73, 48.98, 45.76, 13.48; ESI-MS m/z: 414.3 (M+H)+.

5-methyl-$N^2$-(4-(4-methylpiperazine-1-yl) phenyl)-$N^4$-(benzopyrazine-6-yl)-pyrimidine-2,4-diamine (5e), yellow oil, yield: 68.8%. $^1$H NMR (500 MHz, DMSO-$d_6$) δ 8.90 (s, 1H), 8.86 (s, 1H), 8.79 (d, J=1.5 Hz, 1H), 8.76 (s, 1H), 8.57 (s, 1H), 8.32 (dd, J=9.0, 2.0 Hz, 1H), 8.00 (d, J=9.0 Hz, 1H), 7.96 (s, 1H), 7.53 (d, J=8.5 Hz, 2H), 6.80 (d, J=8.5 Hz, 2H), 3.02 (s, 4H), 2.45 (s, 4H), 2.22 (s, 3H), 2.20 (s, 3H). $^{13}$C NMR (126 MHz, DMSO-$d_6$) δ 158.69, 158.50, 156.56, 145.72, 145.46, 143.27, 143.18, 141.62, 138.81, 133.13, 128.52, 126.27, 120.34, 116.74, 115.96, 105.74, 54.72, 49.02, 45.76, 13.56; ESI-MS m/z: 427.2 (M+H)+.

5-methyl-$N^2$-(4-(4-methylpiperazine-1-yl) phenyl)-$N^4$-(quinoxaline-7-yl)-pyrimidine-2,4-diamine (5f), gray solid, yield: 44.6%. $^1$H NMR (500 MHz, DMSO) δ 8.75 (dd, J=6.0, 2.5 Hz, 2H), 8.53 (s, 1H), 8.50 (s, 1H), 8.11 (d, J=7.5 Hz, 1H), 8.02 (d, J=9.0 Hz, 1H), 7.95-7.89 (m, 2H), 7.45 (t, J=7.0 Hz, 3H), 6.78 (d, J=8.5 Hz, 2H), 3.02 (d, J=4.0 Hz, 4H), 2.45 (d, J=4.5 Hz, 4H), 2.22 (s, 3H), 2.15 (s, 3H). $^{13}$C NMR (126 MHz, DMSO-$d_6$) δ 158.90, 158.62, 156.10, 148.45, 145.88, 144.29, 138.04, 135.31, 133.03, 128.55, 128.27, 125.76, 121.29, 120.98, 116.56, 115.86, 105.31, 54.64, 48.89, 45.67, 13.42; ESI-MS m/z: 426.2 (M+H)+.

5-methyl-$N^2$-(4-(4-methylpiperazine-1-yl)phenyl)-$N^4$-(5,6,7,8-tetrahydronaphthalene-2-yl)-pyrimidine-2,4-diamine (5g), gray solid, yield: 71.2%. $^1$H NMR (400 MHz, DMSO-$d_6$) δ 8.62 (s, 1H), 7.96 (s, 1H), 7.79 (s, 1H), 7.37 (d, J=9.2 Hz, 2H), 7.23-7.14 (m, 2H), 7.08-7.01 (m, 1H), 6.64 (d, J=8.8 Hz, 2H), 3.03-2.95 (m, 4H), 2.83 (s, 2H), 2.61 (s, 2H), 2.51-2.47 (m, 4H), 2.26 (s, 3H), 2.10 (s, 3H), 1.69 (s, 4H). $^{13}$C NMR (126 MHz, DMSO-$d_6$) δ 160.32, 158.46, 154.96, 144.92, 137.86, 137.35, 134.04, 133.50, 126.21, 125.11, 124.56, 118.99, 115.78, 104.01, 54.60, 49.08, 45.78, 29.32, 24.52, 22.43, 22.36, 13.28; ESI-MS m/z: 429.3 (M+H)+.

$N^4$-(2,3-dihydro-1H-indene-5-yl)-5-methyl-$N^2$-(4-(4-methylpiperazine-1-yl)phenyl)pyrimidine-2,4-diamine (5h), yellow oil, yield: 43.4%. $^1$H NMR (400 MHz, DMSO) δ 8.70 (s, 1H), 8.12 (s, 1H), 7.83 (s, 1H), 7.65 (d, J=1.2 Hz, 1H), 7.51 (d, J=9.2 Hz, 2H), 7.38 (dd, J=8.0, 1.6 Hz, 1H), 7.18 (d, J=8.0 Hz, 1H), 6.79 (d, J=9.2 Hz, 2H), 3.07-3.01 (m, 4H), 2.87 (t, J=7.6 Hz, 4H), 2.50-2.45 (m, 4H), 2.24 (s, 3H), 2.10 (s, 3H), 2.05 (dd, J=14.8, 7.6 Hz, 2H). $^{13}$C NMR (126 MHz, DMSO) δ 159.24, 158.51, 155.42, 145.43, 143.59, 138.01, 137.82, 133.56, 123.63, 120.23, 120.00, 118.48, 115.84, 104.63, 54.71, 49.08, 45.73, 32.58, 31.81, 25.29, 13.48; ESI-MS m/z: 415.3 (M+H)+.

5-methyl-$N^4$-(3-methyl-1H-indazol-6-yl)-$N^2$-(4-(4-methylpiperazine-1-yl)phenyl)pyrimidine-2,4-diamine (5i), white solid, yield: 35.4%. $^1$H NMR (500 MHz, DMSO-$d_6$) δ 12.48 (s, 1H), 8.73 (s, 1H), 8.37 (s, 1H), 7.85 (s, 1H), 7.80 (s, 1H), 7.59 (d, J=8.0 Hz, 1H), 7.51 (d, J=7.5 Hz, 2H), 7.36 (d, J=8.0 Hz, 1H), 6.72 (d, J=8.0 Hz, 2H), 3.01 (s, 4H), 2.47 (s, 4H), 2.25 (s, 4H), 2.12 (s, 3H). $^{13}$C NMR (126 MHz, DMSO-$d_6$) δ 159.41, 158.41, 155.63, 145.20, 141.34, 138.09, 133.68, 119.71, 119.10, 118.55, 116.73, 115.95, 105.08, 102.37, 54.45, 48.77, 45.36, 13.52, 11.69; ESI-MS m/z: 429.3 (M+H)+.

Tert-butyl (2-(6-((5-methyl-2-((4-(4-methylpiperazine-1-yl)phenyl) amino)-pyrimidine-4-yl) amino)-2H-indazol-2-yl) ethyl) carbamate (5j), gray solid, yield: 12.7%. $^1$H NMR (500 MHz, DMSO-$d_6$) δ 8.75 (s, 1H), 8.21 (s, 1H), 8.14 (s, 2H), 7.84 (s, 1H), 7.61 (d, J=8.5 Hz, 1H), 7.55 (d, J=8.5 Hz, 1H), 7.28 (d, J=8.0 Hz, 1H), 7.05 (s, 1H), 6.79 (d, J=8.5 Hz, 2H), 4.41 (d, J=6.0 Hz, 2H), 3.49-3.45 (m, 2H), 3.02 (s, 4H), 2.45 (s, 4H), 2.21 (s, 3H), 2.12 (s, 3H), 1.37 (s, 9H). $^{13}$C NMR (126 MHz, DMSO-$d_6$) δ 159.25, 158.53, 155.58, 155.51, 148.76, 145.43, 137.09, 133.50, 123.78, 119.93, 119.78, 119.28, 118.05, 116.03, 107.06, 105.02, 77.95, 54.71, 52.05, 49.09, 45.73, 40.51, 28.17, 13.52; ESI-MS m/z: 558.3 (M+H)+.

5-methyl-$N^4$-(1-methyl-1H-indazol-6-yl)-$N^2$-(4-(4-methylpiperazine-1-yl)phenyl)pyrimidine-2,4-diamine (5k), gray solid, yield: 54.1%. $^1$H NMR (400 MHz, DMSO-$d_6$) δ 8.83 (s, 1H), 8.44 (s, 1H), 8.14 (s, 1H), 7.97 (s, 1H), 7.91 (s, 1H), 7.68 (s, 1H), 7.52 (s, 2H), 7.44 (s, 1H), 6.75 (s, 2H), 3.91 (s, 3H), 3.02 (s, 4H), 2.46 (s, 4H), 2.24 (s, 3H), 2.17 (s, 3H). $^{13}$C NMR (100 MHz, DMSO-$d_6$) δ 159.17, 158.41, 155.84, 145.55, 140.11, 138.42, 133.40, 132.08, 120.14, 119.46, 117.03, 115.78, 105.23, 100.67, 54.71, 48.97, 45.73, 35.20, 13.54; ESI-MS m/z: 429.2 (M+H)+.

Example 3: Chemical Synthesis of Compound 6a-6m

The synthesis route of the compound 6a-6m was as follows:

The general synthesis route was as follows:

2,4-dichloro-5-methylpyrimidine (1d) reacted with 6-aminoindazole to produce an intermediate 2d, and the intermediate 2d and various substituted amines underwent a nucleophilic substitution reaction to generate a final product 6a-6m.

Taking the synthesis of a compound 6a for example, a specific synthesis process was as follows:

Compound 2d was prepared according to Example 1. Compound 2d (259.7 mg, 1 mmol) and 4-(4-methylpiperazine)aniline (191.27 mg, 1 mmol) were dissolved in 4 ml of methanol, then added with (TFA (148.56 v L, 2 mmol), heated to 80° C., and the reaction was monitored by TLC. After the reaction was completed, the mixture was cooled to room temperature, the resulting mixture was adjusted to be neutral with saturated sodium bicarbonate, extracted with ethyl acetate (3×25 mL), washed with saturated salt solution, dried and concentrated by anhydrous $Na_2SO_4$, and a final product 6a was obtained by silica gel column chromatography.

A structure and characterization data of the compound 6a-6m were as follows:

$N^4$-(1H-indazol-6-yl)-5-methyl-$N^2$-(4-morphinophenyl) pyrimidine-2,4-diamine (6a), yellow solid, yield: 33.9%. $^1$H NMR (500 MHz, DMSO-$d_6$) δ 12.89 (s, 1H), 8.72 (s, 1H), 8.35 (s, 1H), 8.00 (s, 1H), 7.86 (s, 1H), 7.82 (s, 1H), 7.67 (d, J=8.5 Hz, 1H), 7.50 (d, J=8.5 Hz, 2H), 7.41 (d, J=8.5 Hz, 1H), 6.70 (d, J=9.0 Hz, 2H), 2.89 (d, J=4.5 Hz, 4H), 2. 82 (d, J=4. 5 Hz, 4H), 2. 12 (s, 3H). $^{13}$C NMR (126 MHz, DMSO-$d_6$) δ 159.35, 158.46, 155.74, 146.12, 140.43, 138.06, 133.52, 133.18, 119.72, 119.17, 117.53, 115.92, 104.99, 102.32, 50.38, 45.62, 13.48; ESI-MS m/z: 402.2 (M+H)$^+$.

$N^4$-(1H-indazol-6-yl)-5-methyl-$N^2$-(4-(piperazine-1-yl) phenyl) py rimidine-2,4-diamine (6b), yellow solid, yield: 29.4%. $^1$H NMR (500 MHz, DMSO-$d_6$) δ 12.89 (s, 1H), 8.72 (s, 1H), 8.35 (s, 1H), 8.00 (s, 1H), 7.86 (s, 1H), 7.82 (s, 1H), 7.67 (d, J=8.5 Hz, 1H), 7.50 (d, J=8.5 Hz, 2H), 7.41 (d, J=8.5 Hz, 1H), 6.70 (d, J=9.0 Hz, 2H), 2.89 (d, J=4.5 Hz, 4H), 2.82 (d, J=4.5 Hz, 4H), 2.12 (s, 3H). $^{13}$C NMR (126 MHz, DMSO-$d_6$) δ 159.35, 158.46, 155.74, 146.12, 140.43, 138.06, 133.52, 133.18, 119.72, 119.17, 117.53, 115.92, 104.99, 102.32, 50.38, 45.62, 13.48; ESI-MS m/z: 402.2 (M+H)>.

$N^2$-(4-(4,4-difluoropiperazine-1-yl)phenyl)-$N^4$-(1H-indazol-6-yl)-5-methylpyrimidine-2,4-diamine (6c), gray solid, yield: 61.1%. $^1$H NMR (500 MHz, DMSO-$d_6$) δ 12.98 (s, 1H), 8.79 (s, 1H), 8.44 (s, 1H), 7.99 (s, 1H), 7.92 (s, 1H), 7.86 (s, 1H), 7.66 (d, J=8.5 Hz, 1H), 7.55 (d, J=9.0 Hz, 2H), 7.44 (d, J=8.5 Hz, 1H), 6.79 (d, J=9.0 Hz, 2H), 3.19-3.10 (m, 4H), 2.14 (s, 3H), 2.07-1.99 (n, 4H). $^{13}$C NMR (126 MHz, DMSO-$d_6$) δ 159.38, 158.36, 155.70, 144.03, 140.58, 140.41, 138.04, 134.15, 133.18, 119.67, 119.14, 117.52, 116.94, 105.19, 102.39, 54.87, 46.85, 33.07, 13.54; ESI-MS m/z: 436.2 (M+H)$^+$.

4-(4-((4-((1H-indazol-6-yl) amino)-5-methylpyrimidine-2-yl) ami no)phenyl)thiomorpholine 1,1-dioxide (6d), gray solid, yield: 81.4%. $^1$H NMR (500 MHz, DMSO-$d_6$) δ 13.00 (s, 1H), 8.83 (s, 1H), 8.45 (s, 1H), 8.01-7.84 (m, 3H), 7.67 (d, J=8.5 Hz, 1H), 7.57 (d, J=8.0 Hz, 2H), 7.43 (d, J=8.0 Hz, 1H), 6.82 (d, J=8.0 Hz, 2H), 3.62 (s, 4H), 3.11 (s, 4H), 2.14 (s, 3H). $^{13}$C NMR (126 MHz, DMSO-$d_6$) δ 159.39, 158.85, 158.29, 155.68, 142.01, 138.02, 134.28, 133.10, 119.84, 119.67, 119.11, 117.52, 116.69, 105.32, 102.49, 49.91, 47.86, 13.56; ESI-MS m/z: 450.2 (M+H)$^+$.

$N^4$-(1H-indazol-6-yl)-$N^2$-(2-methoxy-4-(4-methylpiperazine-1-yl) phenyl)-5-methylpyrimidine-2,4-diamine (6e), gray solid, yield: 26.6%. $^1$H NMR (500 MHz, DMSO-$d_6$) δ 12.92 (s, 1H), 8.45 (s, 1H), 7.98 (s, 1H), 7.91-7.81 (m, 3H), 7.64 (d, J=9.0 Hz, 1H), 7.41 (d, J=8.5 Hz, 1H), 7.26 (s, 1H), 6.61 (s, 1H), 6.31 (d, J=7.5 Hz, 1H), 3.81 (s, 3H), 3.07 (s, 4H), 2.48 (s, 4H), 2.24 (s, 3H), 2.13 (s, 3H). $^{13}$C NMR (126 MHz, DMSO-$d_6$) δ 159.34, 158.44, 155.70, 149.45, 146.79, 140.43, 138.05, 133.17, 121.81, 120.86, 119.72, 119.07, 117.28, 106.97, 105.48, 101.85, 100.14, 55.60, 54.71, 48.97, 45.74, 13.47; ESI-MS m/z: 445.3 (M+H)$^+$.

$N^4$-(1H-indazol-6-yl)-$N^2$-(3-methoxy-4-(4-methylpiperazine-1-yl) phenyl)-5-methylpyrimidine-2,4-diamine (6f), yellow solid, yield: 55.9%. $^1$H NMR (500 MHz, DMSO-$d_6$) δ 12.85 (s, 1H), 8.79 (s, 1H), 8.37 (s, 1H), 7.99 (s, 1H), 7.89 (s, 1H), 7.81 (s, 1H), 7.66 (d, J=8.5 Hz, 1H), 7.40 (d, J=8.5 Hz, 1H), 7.29 (s, 1H), 7. 24 (d, J=9. 5 Hz, 1H), 6. 63 (s, 1H), 3.43 (s, 3H), 2.86 (s, 4H), 2.47 (s, 4H), 2.24 (s, 3H), 2.13 (s, 3H). $^{13}$C NMR (126 MHz, DMSO-$d_6$) δ 159.28, 158.30, 155.70, 151.91, 140.40, 138.05, 136.65, 134.85, 133.21, 119.78, 119.18, 117.76, 117.43, 110.62, 105.47, 103.75, 102.14, 55.01, 54.84, 50.31, 45.84, 13.50; ESI-MS m/z: 445.2 (M+H)>.

$N^4$-(1H-indazol-6-yl)-5-methyl-$N^2$-(4-(4-methylpiperazine-1-yl) p henyl)pyrimidine-2,4-diamine (6g), yellow solid, yield: 29.4%. $^1$H NMR (500 MHz, DMSO-$d_6$) δ 12.93 (s, 1H), 8.93 (s, 1H), 8.55 (s, 1H), 8.01 (s, 1H), 7.84 (d, J=18.5 Hz, 2H), 7.69 (d, J=8.5 Hz, 1H), 7.50 (d, J=9.0 Hz, 2H), 7.41 (d, J=8.0 Hz, 1H), 6.73 (d, J=8.5 Hz, 2H), 3.74-3.67 (m, 4H), 3.01-2.92 (m, 4H), 2.13 (s, 3H). $^{13}$C NMR (126 MHz, DMSO-$d_6$) δ 159.84, 156.85, 152.41, 146.01, 140.31, 137.43, 133.25, 132.61, 120.52, 119.89, 119.51, 117.78, 115.57, 105.57, 103.16, 66.11, 49.26, 13.41; ESI-MS m/z: 401.2 (M+H)$^+$.

$N^2$-(4-(4-ethylpiperazine-1-yl)-2-methoxyphenyl)-$N^4$-(1H-indazol-6-yl)-5-methylpyrimidine-2,4-diamine (6h), white solid, yield: 19.2%. $^1$H NMR (500 MHz, DMSO-$d_6$) δ 12.82 (s, 1H), 8.38 (s, 1H), 7.99 (s, 1H), 7.91-7.82 (m, 3H), 7.65 (d, J=8.5 Hz, 1H), 7.39 (d, J=9.5 Hz, 1H), 7.28 (s, 1H), 6.61 (d, J=2.0 Hz, 1H), 6.31 (d, J=10.0 Hz, 1H), 3.81 (s, 3H), 3.06 (s, 4H), 2.51 (s Hz, 4H), 2.38 (q, J=7.0 Hz, 2H), 2.12 (s, 3H). $^{13}$C NMR (126 MHz, DMSO-$d_6$) δ 159.34, 158.42, 155.69, 149.45, 146.81, 140.40, 138.03, 133.19, 121.81, 120.86, 119.71, 119.06, 117.28, 106.95, 105.47, 101.86, 100.16, 55.61, 52.37, 51.58, 49.06, 13.47, 11.92; ESI-MS m/z: 459.3 (M+H)$^+$.

$N^2$-(4-(4-ethylpiperazine-1-yl)-3-methoxyphenyl)-$N^4$-(1H-indazol-6-yl)-5-methylpyrimidine-2,4-diamine (6i), colorless oil, yield: 61.5%. $^1$H NMR (400 MHz, DMSO-d$_6$) δ 12.90 (s, 1H), 8.82 (s, 1H), 8.42 (s, 1H), 7.99 (s, 1H), 7.89 (s, 1H), 7.85 (s, 1H), 7.64 (d, J=8.4 Hz, 1H), 7.41 (d, J=8.8 Hz, 1H), 7.30 (s, 1H), 7.25 (d, J=8.8 Hz, 1H), 6.63 (d, J=8.8 Hz, 1H), 5.33 (s, 1H), 3.43 (s, 3H), 2.86 (s, 4H), 2.39-2.37 (m, 2H), 2.13 (s, 4H), 1.77 (s, 3H), 1.22 (t, J=6.8 Hz, 1H). $^{13}$C NMR (126 MHz, DMSO-d$_6$) δ 159.29, 158.27, 155.68, 151.90, 140.42, 138.07, 136.66, 134.84, 133.18, 119.74, 119.12, 117.71, 117.39, 110.60, 105.52, 103.74, 102.17, 52.63, 52.07, 51.67, 50.36, 13.53, 11.87; ESI-MS m/z: 459.3 (M+H)$^+$.

$N^4$-(1H-indazol-6-yl)-5-methyl-$N^2$-(4-(4-(4-methylpiperazine-1-y 1)piperidine-1-yl)phenyl)pyrimidine-2,4-diamine (6i), white solid, yield: 73.6%. $^1$H NMR (500 MHz, DMSO-d$_6$) δ 12.89 (s, 1H), 8.71 (s, 1H), 8.35 (s, 1H), 7.99 (s, 1H), 7.84 (d, J=12.5 Hz, 2H), 7.67 (d, J=8.7 Hz, 1H), 7.49 (d, J=8.9 Hz, 2H), 7.42 (d, J=8.6 Hz, 1H), 6.71 (d, J=8.9 Hz, 2H), 3.52 (d, J=12.0 Hz, 2H), 2.54 (s, 1H), 2.30 (s, 4H), 2.26-2.18 (m, 2H), 1.80 (d, J=11.6 Hz, 3H), 1.54-1.42 (n, 3H). $^{13}$C NMR (126 MHz, DMSO-d$_6$) δ 159.35, 158.46, 155.74, 145.54, 138.07, 133.40, 133.21, 119.72, 119.15, 117.51, 116.40, 105.01, 102.28, 83.88, 79.19, 60.85, 55.15, 49.26, 48.54, 45.74, 27.88, 13.51; ESI-MS m/z: 498.3 (M+H)$^+$.

$N^4$-(1H-indazol-6-yl)-$N^2$-(2-methoxy-4-(4-(4-methylpiperazine-1-yl)piperidine-1-yl)phenyl)-5-methylpyrimidine-2,4-diamine (6k).

Yellow solid, 68.9% yield. $^1$H NMR (500 MHz, DMSO-d$_6$) δ 12.83 (s, 1H), 8.38 (s, 1H), 7.98 (s, 1H), 7.85 (d, J=7.0 Hz, 3H), 7.64 (d, J=8.5 Hz, 1H), 7.38 (d, J=8.0 Hz, 1H), 7.27 (s, 1H), 6.60 (s, 1H), 6.31 (d, J=7.0 Hz, 1H), 3.80 (s, 3H), 3.61 (d, J=12.0 Hz, 2H), 2.58 (t, J=11.5 Hz, 3H), 2.36-2.20 (m, 4H), 2.13 (d, J=9.0 Hz, 6H), 1.83 (d, J=11.3 Hz, 2H), 1.56-1.42 (m, 2H). $^{13}$C NMR (126 MHz, DMSO-d$_6$) δ 159.36, 158.47, 155.66, 150.46, 149.64, 146.99, 138.02, 133.30, 121.54, 121.21, 119.78, 119.04, 117.34, 107.47, 105.40, 101.95, 100.62, 60.84, 55.57, 54.98, 49.11, 48.46, 45.63, 27.76, 13.39; ESI-MS m/z: 528.3 (M+H)$^+$. (4-((4-((1H-indazol-6-yl) amino)-5-methylpyrimidine-2-yl) amino) phenyl) (4-methylpiperazine-1-yl)methanone ((6m), colorless liquid, yield: 13.8%. $^1$H NMR (400 MHz, DMSO-d$_6$) δ 9.30 (s, 1H), 8.53 (s, 1H), 7.96 (s, 1H), 7.88 (s, 1H), 7.79 (s, 1H), 7.71 (d, J=8.8 Hz, 2H), 7.64 (d, J=8.4 Hz, 1H), 7.33 (d, J=8.8 Hz, 1H), 7.11 (d, J=8. 8 Hz, 2H), 2. 84 (s, 4H), 2. 44 (s, 4H), 2.10 (s, 3H), 1.70 (s, 3H). $^{13}$C NMR (126 MHz, DMSO-d$_6$) δ 169.22, 159.54, 157.86, 155.63, 142.65, 140.46, 137.79, 133.12, 127.81, 126.85, 119.73, 119.34, 117.88, 117.29, 106.37, 103.04, 54.55, 53.86, 45.59, 13.57; ESI-MS m/z: 473.2 (M+H)$^+$.

(4-((4-((1H-indazol-6-yl)amino)-5-methylpyrimidine-2-yl)amino)-N-(2-morpholinoethyl)benzamide (6n), white solid, yield: 60.2%. $^1$H NMR (500 MHz, DMSO-d$_6$) δ 13.02 (s, 1H), 9.33 (s, 1H), 8.59 (s, 1H), 8.24 (s, 1H), 8.15-7.88 (m, 3H), 7.79 (d, J=8.0 Hz, 2H), 7.71 (d, J=8.5 Hz, 1H), 7.63 (d, J=8.0 Hz, 2H), 7.46 (d, J=8.0 Hz, 1H), 3.57 (s, 4H), 2.43 (d, J=13.5 Hz, 6H), 2.17 (s, 3H). $^{13}$C NMR (126 MHz, DMSO-d$_6$) δ 165.92, 159.44, 157.76, 155.56, 143.90, 140.41, 137.84, 133.18, 127.69, 125.85, 119.69, 119.25, 117.63, 116.65, 102.50, 66.14, 57.44, 53.26, 36.35, 13.64; ESI-MS m/z: 473.2 (M+H)$^+$.

Example 4: Kinase (PDGFRα, PDGFRβ, ABL1 and FLT3) Inhibition Test of Compounds The method adopted in the test was Caliper Mobility Shift Assay, which was a detection platform based on the mobility detection technology of microfluidic chip technology. Test steps: 1.25× kinase reaction buffer (62.5 mmol/L HEPES, pH 7.5; 0.001875% Brij-35; 12.5 mmol/L MgCl$_2$; 2.5 mM DTT) and kinase reaction stop solution (100 mmol/L HEPES, pH 7.5; 0.015% Brij-35; 0.2% Coating Reagent #3) were configured. 10 μL of 2.5× kinase solution (adding kinase in 1.25× kinase reaction buffer) was added into 5 μL of compound solution with 5× concentration (dissolved in DMSO, diluted 10 times with water), incubated at room temperature for 10 minutes, then added with 10 μL of 2.5× substrate peptide solution (adding FAM labeled peptide and ATP in 1.25× kinase reaction buffer), reacted at 28° C. for a specific time, and then added with 25 μL of kinase reaction stop solution. Collected data was tested on Caliper to yield that inhibition ratio to kinase activity=(max−conversion)/(max−min)×100. "max" was DMSO control without adding compound, and "min" was low control. When IC$_{50}$ was determined, each sample was provided with 10 dilutions, each with 2 multiple holes, and repeated for 3 times. The results were shown in Table 1.

TABLE 1

Chemical structures of the synthesized compounds and inhibitory rates thereof (%) on PDGFR α, PDGFR β, ABL1 and FLT3 kinases at a concentration of 100 nM

| Serial number | Compound | PDGFR-α | PDGFR-β | ABL1 | FLT3 |
|---|---|---|---|---|---|
| 1 | 3a | 87.1 | 94.4 | 90.4 | 87.5 |
| 2 | 3b | 93.7 | 95.8 | 95.1 | 90.2 |
| 3 | 3c | 62.3 | 81.0 | 84.2 | 78.6 |
| 4 | 3d | 94.2 | 99.6 | 95.2 | 90.5 |
| 5 | 3e | 32.9 | 55.0 | 54.3 | 51.2 |
| 6 | 3f | 1.3 | 3.5 | 4.3 | 34.8 |
| 7 | 3g | 6.0 | 7.2 | 6.9 | 14.6 |
| 8 | 3h | 3.2 | 21.2 | 5.9 | 13.8 |
| 9 | 3i | 6.6 | 30.7 | 23.6 | 42.6 |
| 10 | 5a | 57.3 | 78.6 | 58.9 | 60.3 |
| 11 | 5b | 66.1 | 90.3 | 78.8 | 60.9 |
| 12 | 5c | 67.7 | 79.2 | 58.9 | 65.4 |
| 13 | 5d | 59.1 | 84.1 | 80.9 | 80.4 |
| 14 | 5e | 57.8 | 74.1 | 65.5 | 69.8 |
| 15 | 5f | 82.5 | 91.0 | 90.2 | 90.5 |
| 16 | 5h | 71.8 | 88.9 | 80.2 | 87.1 |
| 17 | 5g | 78.3 | 90.4 | 89.2 | 85.7 |
| 18 | 5j | 60.6 | 71.1 | 71.6 | 74.3 |
| 19 | 5k | 91.1 | 96.4 | 90.4 | 88.7 |
| 20 | 5i | 94.5 | 98.0 | 85.2 | 93.4 |
| 21 | 6a | 84.4 | 93.8 | 98.2 | 87.2 |
| 22 | 6b | 55.0 | 68.7 | 91.2 | 87.3 |
| 23 | 6c | 48.9 | 48.5 | 50.6 | 74.6 |
| 24 | 6d | 66.6 | 70.3 | 59.6 | 78.4 |
| 25 | 6e | 64.8 | 63.4 | 78.8 | 79.5 |
| 26 | 6f | 94.4 | 97.0 | 98.0 | 97.8 |
| 27 | 6g | 87.7 | 93.8 | 89.6 | 87.6 |
| 28 | 6h | 69.3 | 80.2 | 87.5 | 82.6 |
| 29 | 6i | 97.5 | 99.8 | 95.3 | 98.9 |
| 30 | 6j | 82.5 | 85.4 | 87.6 | 91.0 |
| 31 | 6k | 65.0 | 76.4 | 47.5 | 58.4 |
| 32 | 6m | 66.8 | 78.4 | 81.0 | 85.6 |
| 33 | 6n | 80.5 | 82.4 | 81.2 | 82.3 |
| 34 | Pazopanib | 96.9 | 76.7 | 75.3 | 80.6 |

TABLE 2

IC$_{50}$ values of some active compounds inhibiting PDGFR α and PDGFR β kinases

| Serial number | Compound number | IC$_{50}$ (nM) | |
|---|---|---|---|
| | | PDGFR-α | PDGFR-β |
| 1 | 5k | 19 | 7.3 |
| 2 | 5i | 15 | 7.9 |
| 3 | 6a | 17 | 4.2 |
| 4 | 6b | 55 | 68.7 |
| 5 | 6c | 81 | 103 |
| 6 | 6d | 66.6 | 70.3 |
| 7 | 6e | 54 | 72 |
| 8 | 6f | 7.4 | 2.6 |
| 9 | 6g | 19 | 8.8 |
| 10 | 6h | 74 | 40 |
| 11 | 6i | 2.7 | 1.7 |
| 12 | 6j | 15 | 12 |
| 13 | 6n | 20 | 19 |

TABLE 3

IC$_{50}$ values of some compounds inhibiting related kinases

| Serial number | Compound number | IC$_{50}$ (nM) | | | | |
|---|---|---|---|---|---|---|
| | | FGFR2 | PDGFR-α | PDGFR-β | ALK | JAK1 | IKK β |
| 1 | 6d | 117 | 46 | 39 | 186 | 99 | 619 |
| 2 | 6e | >1000 | 54 | 72 | 7.0 | 199 | >1000 |
| 3 | 6j | 89 | 15 | 12 | 23 | 14 | >1000 |
| 4 | 6c | 540 | 81 | 103 | 476 | 72 | >1000 |
| 5 | 6g | 81 | 19 | 8.8 | 26 | 13 | 595 |
| 6 | 6n | 102 | 20 | 19 | 95 | 6.0 | 181 |
| 7 | 6i | 27 | 2.7 | 1.7 | 5.0 | 7.7 | 694 |
| 8 | 6f | 61 | 7.4 | 2.6 | 11 | 31 | >1000 |
| 9 | 6h | >1000 | 74 | 40 | 5.8 | 320 | >1000 |

The results showed that 10 active compounds could effectively inhibit the PDGFRα and PDGFRβ kinases, but have relatively weak inhibitory activity on other kinases, indicating good kinase selectivity. In particular, the compounds 6g, 6i and 6f had significant inhibitory activities on PDGFRα and PDGFRβ wherein the compound 6i had the strongest inhibitory activity.

Example 5: Kinase Selectivity Test of Active Compounds

According to the above-mentioned method for measuring kinase inhibitory activity, the inhibitory activity of the active compounds on other multiple kinases was measured to characterize the kinase selectivity of active inhibitors.

TABLE 4

Selective inhibitory activity of the active compound 6i on 16 kinases at a concentration of 100 nM Compounds % inhibition @ 100 nM

| | 6i (% inhibition @ 100 nM) | | | |
|---|---|---|---|---|
| Kinase | % inhibition 1 | % inhibition 2 | Average % inhibition | SD |
| EGFR | 40.9 | 43.6 | 42.3 | 1.9 |
| EGFR L858R/T790M/C797S | 73.4 | 75.7 | 74.5 | 1.6 |
| EGFR T790M | 57.0 | 56.8 | 56.9 | 0.1 |
| FLT1 | 78.7 | 80.7 | 79.7 | 1.5 |
| JAK1 | 91.7 | 89.3 | 90.5 | 1.7 |
| FGFR3 | 8.1 | 13.7 | 10.9 | 4.0 |
| KDR | 71.5 | 71.3 | 71.4 | 0.2 |
| EGFR/T790M/L858R | 76.6 | 77.9 | 77.2 | 0.9 |
| EGFR L858R | 61.7 | 62.6 | 62.1 | 0.6 |
| FGFR1 | 65.0 | 66.6 | 65.8 | 1.1 |
| BTK | 49.1 | 51.3 | 50.2 | 1.6 |
| FGFR2 | 83.85 | 82.11 | 83.0 | 1.2 |
| PDGFR α | 98.91 | 103.00 | 101.0 | 2.9 |
| PDGFR β | 100.98 | 102.53 | 101.8 | 1.1 |
| SRC | 90.98 | 93.47 | 92.2 | 1.8 |

The results showed that the active compound 6i could effectively inhibit the PDGFRα and PDGFRβ kinases at the concentration of 100 nM, wherein the inhibition rate could be over 100%, but had relatively weak inhibitory activity on other kinases, indicating good kinase selectivity.

Example 6 Inhibition Test of Active Compounds on Osteosarcoma Cells

Logarithmic osteosarcoma cells were inoculated into a 96-well plate with a cell concentration of 1,500 cell/well for 6 hours by using MTT assay, and each well was filled with 200 μL of cell suspension. Samples were prepared into solutions with 5 concentration gradients of 0.5, 2.5, 5, 10 and 25 μmol/L, and each sample was equipped with 5 multiple holes. The samples were cultured in an incubator for 48 hours (37° C., 5% CO$_2$), and 20 v L of MTT (3-(4,5-dimethylthiazole-2)-2,5-diphenyltetrazole) were added into each hole. After continuous culture for 4 hours, the culture solution was discarded by suction, and 200 v L of DMSO were added to each well. After shaking and dissolving for 10 minutes, OD values of each well were measured at 490 nM with a multifunctional microplate reader and the inhibition rate was calculated. Calculation method of IC$_{50}$ value: the IC$_{50}$ values of the samples were calculated by curve fitting with GraphPad Prism software.

TABLE 5

Inhibitory activity (IC$^{50}$) of active compounds on four osteosarcoma cells determined by MTT assay

| | MG-63* | U2OS | SAOS-2 | MNNG/HOS |
|---|---|---|---|---|
| Pazopanib# | >100 μM | >100 μM | >100 μM | 8.52 ± 0.868 μM |
| Axitinib# | >100 μM | >100 μM | 35.14 ± 0.253 μM | 7.47 ± 0.202 μM |
| Imatinib# | 31.69 ± 0.703 μM | 27.15 ± 0.605 μM | 15.01 ± 0.064 μM | 20.5 ± 0.808 μM |
| 6f | 0.841 ± 0.005 μM | 0.756 ± 0.001 μM | 0.72 ± 0.025 μM | 1.36 ± 0.019 μM |
| 6g | 0.958 ± 0.007 μM | 0.552 ± 0.0023 μM | 0.95 ± 0.001 μM | 1.4 ± 0.003 |
| 6i | 0.438 ± 0.001 μM | 0.418 ± 0.017 μM | 0.37 ± 0.002 μM | 1.03 ± 0.08 μM |

The results showed that three active compounds had strong inhibitory activities on the proliferation of four osteosarcoma cell lines compared with three positive drugs, indicating that these compounds had excellent anti-osteosarcoma effects.

Example 7: Adhesion and Metastasis Test of Active Compound 6i Inhibiting Osteosarcoma Cells Human Plasma Fibronectin was pre-incubated in a 96-well plate, and inoculated with osteosarcoma cells subjected to the effects of 0, 0.1, 0.2 and 0.4 µM of 6i, 0.4 µM of Pazopanib, and 0.4 µM of Imatinib for 48 hours, with $5 \times 10^4$ cells per well, and each group was provided with 6 multiple wells, and cultured in 5% $CO_2$ at 37° C. for 40 minutes, washed with PBS to remove non-adhered cells, fixed with 4% paraformaldehyde at room temperature for 15 minutes and 100 µL, washed with 200 µL of PBS for three times, then the PBS was discarded, and each well was dyed with 50 µL of crystal violet for 5 minutes at room temperature, washed with 200 µL of ultrapure water for three times after dyeing, then the ultrapure water was discarded. Each well was dried, and added with 100 µL of 33% glacial acetic acid and the crystal violet was dissolved by shaking for 10 minutes. The absorbance was measured by a microplate reader at 570 nM, and the adhesion rate (%)=(OD value of tumor cells in the drug-added treated group–Hu FN OD value)/(OD value of untreated tumor cells–Hu FN OD value)×100%.

Osteosarcoma cells with a density of $5 \times 10^4$ cells (treated with 0, 0.1, 0.2 and 0.4 µM of 6i, 0.4 of µM Pazopanib, and 0.4 µM of Imatinib) after 48 hours were inoculated into a 6-well plate, RMPL 1640 culture medium containing 10% serum was added and placed in an incubator to make the cells adhere to the wall to form monolayer cells, and a "+" cross scratch was made with a 200 µL pipette tip. The cells were washed with sterile PBS for three times, and basal medium containing 2.5 µL of TCS was added respectively. Photographs were taken at 0 hour, 24 hours and 48 hours under an inverted microscope, and migration distances were measured with Imag J software.

Figure 1:
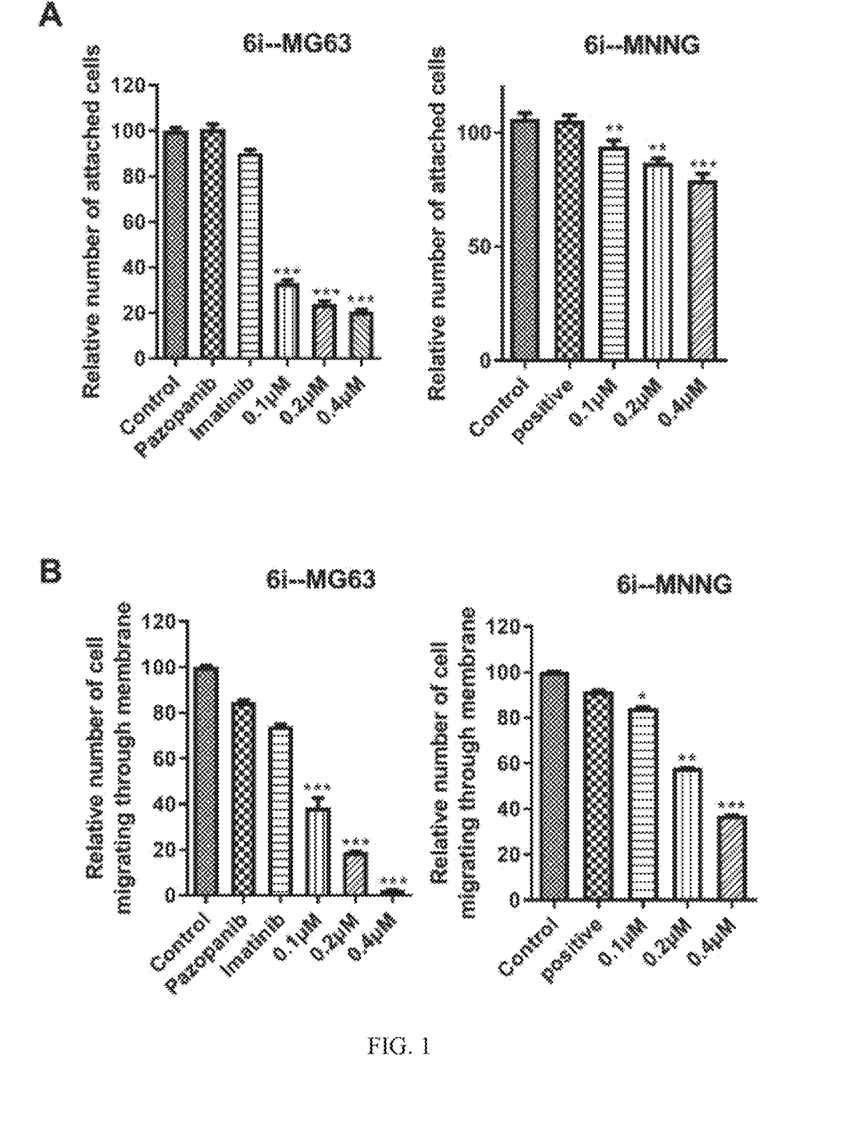
FIG. 1 shows experimental results of inhibiting adhesion and metastasis of osteosarcoma cells by an active compound 6i in Example 7.

The results were shown in FIG. 1. The results showed that 0.1, 0.2 and 0.4 uM of active compound 6i had strong dose-dependent inhibitory activity on the adhesion (4A) and metastasis (4B) of osteosarcoma cells MG63 and MNNG compared with the positive drugs.

Example 8: Inhibitory Activity of Active Compound 6i on Two Osteosarcoma Cells PDGFR Signaling Pathway Related Proteins After pretreating the osteosarcoma cell line with the compound for 48 hours, the culture medium was sucked off, washed with PBS for 3 times, and the total protein was extracted after lysis. A phosphorylation level of the PDGFR signaling pathway related proteins was detected by Western Blot.

Figure 2:
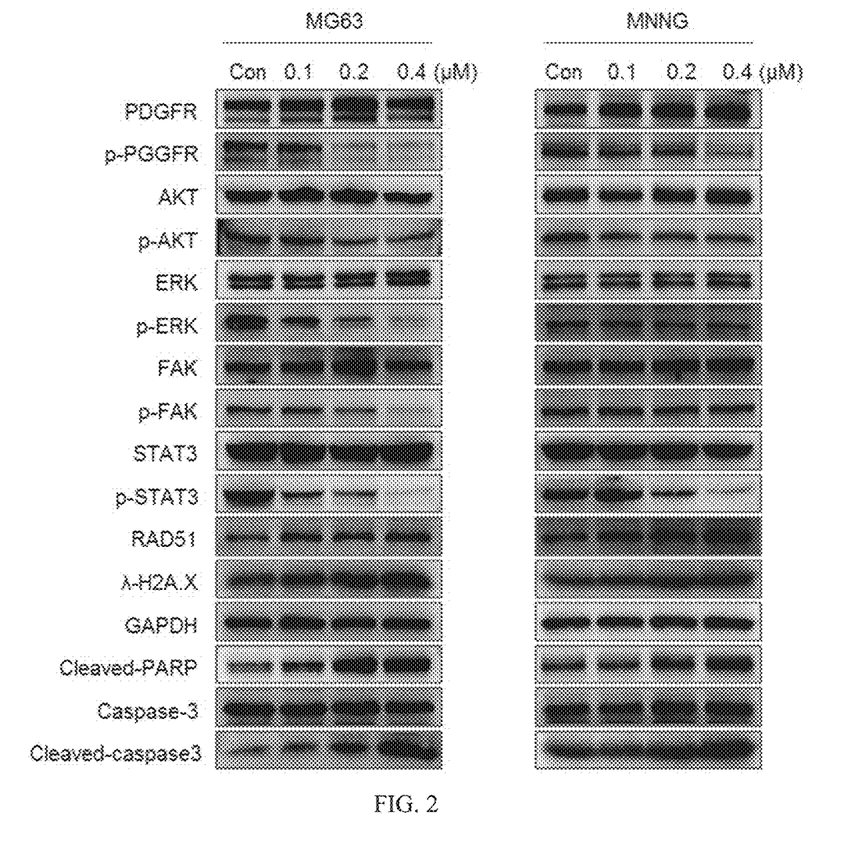
FIG. 2 shows inhibitory activity of the active compound 6i in Example 8 on two osteosarcoma cell PDGFR signaling pathway related proteins.

The results were shown in FIG. 2. The results showed that 0.1, 0.2 and 0.4 uM of active compound 6i had strong dose-dependent inhibition of phosphorylation of osteosarcoma cells MG63 and MNNG related signaling pathway proteins compared with positive drugs.

Example 9: Inhibitory Activity Test of Active Compounds on Two Human Neovascular Cells The same MTT assay as in Example 6 was used to determine the inhibitory activity of the active compound 6i on two retinal cells.

TABLE 6

Inhibitory activity ($IC_{50}$, uM) of active compounds on three human retinal cells determined by MTT assay

| Compounds | ARPE-19 | HCMEC-D3 | HBVP |
|---|---|---|---|
| 6i | 17.48 ± 0.37 | 0.23 ± 0.002 | 0.55 ± 0.098 |
| Sorafenib | 23.29 ± 0.143 | 6.32 ± 0.73 | 9.92 ± 0.598 |
| Vorolanib | 56.23 ± 3.23 | 34.32 ± 0.885 | 18.5 ± 10.520 |
| Imatinib | 40.33 ± 1.662 | 44.89 ± 1.366 | 15.15 ± 1.088 |

The results showed that the active compound 6i had strong inhibitory activity on human immortalized human brain microvascular endothelial cells (HCMEC/D3) and human cerebrovascular pericytes (HBVP) compared with multiple positive drugs, but had almost no inhibitory activity on human normal retinal cells ARPE-19 at low concentration, which indicated that the active compound 6i could effectively inhibit fundus vascular proliferation, thus alleviating ophthalmic diseases wet age-related macular degeneration or uveitis, and had low toxicity.

We claim:
1. A pyrimidine small-molecule compound, wherein a structural formula of the pyrimidine small-molecule compound is selected from the group consisting of the following:

-continued

-continued

* * * * *